(12) United States Patent
Arbiser

(10) Patent No.: US 8,030,299 B2
(45) Date of Patent: Oct. 4, 2011

(54) PALLADIUM COMPLEXES INHIBIT N-MYRISTOYLTRANSFERASE ACTIVITY IN VITRO AND CANCER GROWTH IN VIVO

(76) Inventor: Jack Arbiser, Atlanta, GA (US)

( * ) Notice: Subject to any disclaimer, the term of this patent is extended or adjusted under 35 U.S.C. 154(b) by 100 days.

(21) Appl. No.: 12/470,008

(22) Filed: May 21, 2009

(65) Prior Publication Data

US 2010/0076076 A1    Mar. 25, 2010

Related U.S. Application Data

(63) Continuation of application No. PCT/US2007/087741, filed on Dec. 17, 2007.

(60) Provisional application No. 60/875,517, filed on Dec. 18, 2006.

(51) Int. Cl.
*A61K 31/43* (2006.01)
*A61K 33/26* (2006.01)
*A01N 59/16* (2006.01)

(52) U.S. Cl. ........... 514/192; 424/646
(58) Field of Classification Search ........... 514/192; 424/646
See application file for complete search history.

(56) References Cited

U.S. PATENT DOCUMENTS

| | | | |
|---|---|---|---|
| 5,679,697 A | 10/1997 | Garnett et al. | |
| 5,880,149 A | 3/1999 | Grinstaff et al. | |
| 6,462,075 B1 | 10/2002 | Bowen et al. | |
| 6,664,272 B2 | 12/2003 | Snyder et al. | |
| 6,673,843 B2 | 1/2004 | Arbiser | |
| 2004/0176384 A1 | 9/2004 | Snyder et al. | |
| 2005/0148599 A1 | 7/2005 | Bowen et al. | |
| 2006/0106100 A1 | 5/2006 | Caires et al. | |

OTHER PUBLICATIONS

Bauland et. al., Plastic and Reconstructive Surgery, 2006, American Society of Plastic Surgeons, vol. 117, issue 2, pp. 29e-35e.*
de Villiers et. al., Virology, 2004, Elsevier, vol. 324, pp. 17-27.*
Miller et. al., The New England Journal of Medicine, 2006, Massachusetts Medical Society, vol. 355, issue 1, pp. 51-65.*
Rindfleisch et. al., American Family Physician, 2005, American Academy of Family Physicians, vol. 72, No. 6, pp. 1037-1047.*
Ahmadzadeh,M. and Rosenberg,S.A. IL-2 administration increases CD4+ CD25(hi) Foxp3+ regulatory T cells in cancer patients, Blood, 107: 2409-2414, 2006.
Arbiser et al., The antiangiogenic agents TNP-470 and 2-methoxyestradiol inhibit the growth of angiosarcoma in mice, J. Am. Acad. Derm. pp. 925-929 (Jun. 1999).
Arbiser,J.L., et al., Oncogenic H-ras stimulates tumor angiogenesis by two distinct pathways, Proc.Natl.Acad.Sci.U.S.A, 94: 861-866, 1997.
Arbiser,J.L. Molecular regulation of angiogenesis and tumorigenesis by signal transduction pathways: evidence of predictable and reproducible patterns of synergy in diverse neoplasms, Semin.Cancer Biol., 14: 81-91, 2004.
Arbiser,J.L., et al., Curcumin is an in vivo inhibitor of angiogenesis, Mol.Med., 4: 376-383, 1998.
Atkins,M.B. Cytokine-based therapy and biochemotherapy for advanced melanoma, Clin.Cancer Res., 12: 2353s-2358s, 2006.
Bai,X., et al., Honokiol, a small molecular weight natural product, inhibits angiogenesis in vitro and tumor growth in vivo, J.Biol. Chem., 278: 35501-35507, 2003.
Bhoumik,A., et al., Inhibition of melanoma growth and metastasis by ATF2-derived peptides, Cancer Res., 64: 8222-8230, 2004.
Bromberg,J. Stat proteins and oncogenesis, J.Clin.Invest, 109: 1139-1142, 2002.
Budakoti, A. et al., "Syntheses, characterization and in vitro antiamoebic activity of new Pd(II) complexes with 1 N-substituted thiocarbamoyl-3,5-diphenyl-2-pyrazoline derivatives," Eur. J. Med. Chem. 42(4):544-51 (2007).
Budakoti, A. et al., "Synthesis and antiamoebic activity of new 1-n-substituted thiocarbamoyl-3,5-diphenyl-2-pyrazoline derivatives and their Pd(II) complexes," Eur. J. Medicinal Chem. 41:63-70 (2006).
Burdelya, L., et al., Stat3 activity in melanoma cells affects migration of immune effector cells and nitric oxide-mediated antitumor effects, J.Immunol., 174: 3925-3931, 2005.
Cerimele, F., et al., Reactive oxygen signaling and MAPK activation distinguish Epstein-Barr Virus (EBV)-positive versus EBV-negative Burkitt's lymphoma, Proc.Natl.Acad.Sci.U.S.A, 102: 175-179, 2005.
Cohen, C., et al., Mitogen-actived protein kinase activation is an early event in melanoma progression, Clin.Cancer Res., 8: 3728-3733, 2002.
Dhawan,P. and Richmond, A. A novel NF-kappa B-inducing kinase-MAPK signaling pathway up-regulates NF-kappa B activity in melanoma cells, J.Biol.Chem., 277: 7920-7928, 2002.
Dhawan, P., et al., Constitutive activation of Akt/protein kinase B in melanoma leads to up-regulation of nuclear factor-kappaB and tumor progression, Cancer Res., 62: 7335-7342, 2002.

(Continued)

*Primary Examiner* — Sreeni Padmanabhan
*Assistant Examiner* — Sarah Pihonak
(74) *Attorney, Agent, or Firm* — Nutter McClennen & Fish LLP; William C. Geary, III

(57) ABSTRACT

Melanoma is a solid tumor that is notoriously resistant to chemotherapy, and its incidence is rapidly increasing. Recently, several signaling pathways have been demonstrated to contribute to melanoma tumorigenesis, including constitutive activation of MAP kinase, Akt and stat-3. The activation of multiple pathways may account in part for the difficulty in treatment of melanoma. In a recent screen of compounds, we found that an organopalladium complex showed significant antiproliferative activity against melanoma cells. This complex, tris(dibenzylideneacetone)dipalladium (Tris DBA), has activity against B16 murine and A375 human melanoma in vivo. Tris DBA inhibits several signaling pathways including activation of MAP kinase, Akt, stat-3 and S6 kinase activation. Tris(dibenzylideneacetone)dipalladium is thus a novel compound that is a member of a class of noble metal complexes with potential antitumor activity. Further preclinical evaluation of TrisDBA and related complexes is warranted.

8 Claims, 5 Drawing Sheets

OTHER PUBLICATIONS

Eisen,T., et al., Sorafenib in advanced melanoma: a Phase II randomised discontinuation trial analysis, Br.J.Cancer 95:581-86 (2006).

Eton, O. et al., A phase II study of "decrescendo" interleukin-2 plus interferon-a-2a in patients with progressive metastic melanoma after chemotherapy, Cancer 88(7):1703-09 (2000).

Fried, L. et al., "The reactive oxygen-driven tumor: relevance to melanoma," The Authors, J. Compilation, Pigment Cell Melanoma Res. (2008).

Gabrilovich,D.I., et al., Production of vascular endothelial growth factor by human tumors inhibits the functional maturation of dendritic cells, Nat.Med., 2: 1096-1103, 1996.

Garraway, L.A., et al., Integrative genomic analyses identify MITF as a lineage survival oncogene amplified in malignant melanoma, Nature, 436: 117-122, 2005.

Govindarajan, B., et al., Malignant transformation of melanocytes to melanoma by constitutive activation of mitogen-activated protein kinase kinase (MAPKK) signaling, J. Biol. Chem. 278:9790-95 (2003).

Govindarajan, B., et al., "Overexpression of Akt converts radial growth melanoma to vertical growth melanoma," JCI Online First, publ. online http://www.jci.org (Feb. 22, 2007).

Haluska,F.G., et al., Genetic alterations in signaling pathways in melanoma, Clin.Cancer Res., 12: 2301s-2307s, 2006.

Hamilton,A.L., et al., Proteasome inhibition with bortezomib (PS-341): a phase I study with pharmacodynamic end points using a day 1 and day 4 schedule in a 14-day cycle, J.Clin.Oncol., 23: 6107-6116, 2005.

Huang,S., et al., Level of interleukin-8 expression by metastatic human melanoma cells directly correlates with constitutive NF-kappaB activity, Cytokines Cell Mol.Ther., 6: 9-17, 2000.

International Preliminary Report on Patentability from corresponding PCT/US07/87741, mailed Jul. 2, 2009.

International Search Report from corresponding PCT/US07/87741, mailed May 1, 2008.

John, VD et al., "Antitumour activity of synthetic curcuminoid analogues (1,7-diary-1,6-heptadiene-3,5-diones) and their copper complexes," Appl. Organometallic Chem. 20(8):477-82 (2006).

Karakousis,C.P. et al., cis-Dichlorodiammineplatinum(II) and DTIC in malignant melanoma, Cancer Treat.Rep., 63: 2009-2010, 1979.

Karakousis,C.P. et al., "Tourniquet infusion chemotherapy for extremity in-transit lesions in malignant melanoma," Ann. surg. Onc. 4(6):506-10 (1997).

Khor,T.O., et al., Combined inhibitory effects of curcumin and phenethyl isothiocyanate on the growth of human PC-3 prostate xenografts in immunodeficient mice, Cancer Res., 66: 613-621, 2006.

King, M.J., and Sharma, R.K. N-myristoyl transferase assay using phosphocellulose paper binding. Anal. Biochem., 199: 149-153, 1991.

King, M.J. and Sharma, R.K. (1993) Identification, purification and characterization of a membrane-associated N-myristoyltransferase inhibitor protein from bovine brain. Biochem. J. 291, 635-639.

Legha, S.S. Durable complete responses in metastatic melanoma treated with interleukin-2 in combination with interferon alpha and chemotherapy, Semin.Oncol., 24: S39-S43, 1997.

Larribere,L., Khaled,M., Tartare-Deckert,S., Busca,R., Luciano,F., Bille,K., Valony,G., Eychene, A., et al., PI3K mediates protection against TRAIL-induced apoptosis in primary human melanocytes, Cell Death.Differ., 11: 1084-1091, 2004.

Lewis, K.D., et al., A phase II study of biochemotherapy for advanced melanoma incorporating temozolomide, decrescendo interleukin-2 and GM-CSF, Cancer Invest, 23: 303-308, 2005.

Lewis, 'Phase II multicenter study of neoadjuvant biochemotherapy for patients with stage III malignant melanoma, J. Clin. Oncology 24(19):3157-63 (2006).

Liu, A., et al., PSK and Trx80 inhibit B-cell growth in EBV-infected cord blood mononuclear cells through T cells activated by the monocyte products IL-15 and IL-12, Blood, 105: 1606-1613, 2005.

Maker, A.V., et al., Intrapatient dose escalation of anti-CTLA-4 antibody in patients with metastatic melanoma, J.Immunother., 29: 455-463, 2006.

Margolin, K.A., et al., Phase II trial of biochemotherapy with interferon alpha, dacarbazine, cisplatin and tamoxifen in metastatic melanoma: a Southwest Oncology Group trial, J.Cancer Res.Clin.Oncol., 125: 292-296, 1999.

Margolin,K., et al., CCI-779 in metastatic melanoma: a phase II trial of the California Cancer Consortium, Cancer, 104: 1045-1048, 2005.

Markovic,S.N. et al., A phase II study of bortezomib in the treatment of metastatic malignant melanoma, Cancer, 103: 2584-2589, 2005.

Mullally, JE et al., "Pharmacophore model for novel inhibitors of ubiquitin isopeptidases that induce p53-independent cell death," Molecular Pharmacology 62(2):351-58 (2002).

O'Reilly, F.M. et al., Microphthalmia transcription factor immunohistochemistry: a useful diagnostic marker in the diagnosis and detection of cutaneous melanoma, sentinel lymph node metastases, and extracutaneous melanocytic neoplasms, J.Am.Acad.Dermatol., 45: 414-419, 2001.

Oyama,T. et al., Vascular endothelial growth factor affects dendritic cell maturation through the inhibition of nuclear factor-kappa B activation in hemopoietic progenitor cells, J.Immunol., 160: 1224-1232, 1998.

Pollock, P.M. and Meltzer, P.S. A genome-based strategy uncovers frequent BRAF mutations in melanoma, Cancer Cell, 2: 5-7, 2002.

Pollock, P.M. et al., High frequency of BRAF mutations in nevi, Nat.Genet., 33: 19-20, 2003.

Raju, R.V. et al., Overexpression of human N-myristoyltransferase utilizing a T7 polymerase gene expression system. Protein Expr. Purif., 7: 431-437, 1996.

Reddy, K. et al., "The antidepressant sertraline downregulates Akt and has activity against melanoma cells," Pigment Cell Melanoma Res. 21:451-56 (2008).

Robinson, T.P. et al., Design, synthesis, and biological evaluation of angiogenesis inhibitors: aromatic enone and dienone analogues of curcumin, Bioorg.Med.Chem.Lett., 13: 115-117, 2003.

Robinson, T. et al., "Synthesis and biological evaluation of aromatic enones related to curcumin," Bioorganic & Medicinal Chem. 13:4007-13 (2005).

Sarbassov, D.D. et al.,A novel binding partner of mTOR, defines a rapamycin-insensitive and raptor-independent pathway that regulates the cytoskeleton, Curr.Biol., 14: 1296-1302, 2004.

Satyamoorthy, K., et al., Insulin-like growth factor-1 induces survival and growth of biologically early melanoma cells through both the mitogen-activated protein kinase and beta-catenin pathways, Cancer Res., 61: 7318-7324, 2001.

Selzer,E. et al. Betulinic acid-induced Mcl-1 expression in human melanoma-mode of action and functional significance, Mol.Med., 8: 877-884, 2002.

Sharma, A. et al., Mutant V599EB-Raf regulates growth and vascular development of malignant melanoma tumors, Cancer Res., 65: 2412-2421, 2005.

Shattuck-Brandt,R.L. and Richmond,A. Enhanced degradation of I-kappaB alpha contributes to endogenous activation of NF-kappaB in Hs294T melanoma cells, Cancer Res., 57: 3032-3039, 1997.

Soengas, M.S. et al., Apaf-1 expression in malignant melanoma, Cell Death.Differ., 13: 352-353, 2006.

Somasundaram, S. et al., Dietary curcumin inhibits chemotherapy-induced apoptosis in models of human breast cancer, Cancer Res., 62: 3868-3875, 2002.

Teng,D.H. et al., MMAC1/PTEN mutations in primary tumor specimens and tumor cell lines, Cancer Res., 57: 5221-5225, 1997.

Tsao,H. et al., Identification of PTEN/MMAC1 alterations in uncultured melanomas and melanoma cell lines, Oncogene, 16: 3397-3402, 1998.

Tuveson,D.A. et al., BRAF as a potential therapeutic target in melanoma and other malignancies, Cancer Cell, 4: 95-98, 2003.

EP Extended Search Report, from EP 07855204.9, mailed Mar. 30, 2010.

Furness, M. et al., "Antiangiogenic agents: studies on fumagillin and curcumin analogs," Curr. Pharma. Design 2005 NL, 11(3):357-73 (2005).

* cited by examiner

Figure 1: Tris(dibenzylideneacetone)dipalladium inhibits angiogenesis in vitro.

Figure 2: Western blot analysis using Phosphorylated forms of MAPK, Akt (a), p70 S6kinase (b), Stat-3 (c)

Figure 3: Treatment of B16 and A375 cells with 10μg/ml of Tris(dibenzylideneacetone)dipalladium decreases levels of VEGF mRNA (corrected for 18S RNA).

Figure 4: Effect of Tris(dba)dipalladium in melanomas *in vivo*.

PALLADIUM COMPLEXES INHIBIT N-MYRISTOYLTRANSFERASE ACTIVITY IN VITRO AND CANCER GROWTH IN VIVO

CROSS REFERENCE TO RELATED APPLICATIONS

This application is a continuation of PCT Application No. PCT/US2007/087741, filed Dec. 17, 2007, entitled "Novel Palladium Complexes Inhibit N-Myristoyltransferase Activity in Vitro and Cancer Growth in Vivo," which claims the benefit of U.S. Provisional Application No. 60/875,517, filed on Dec. 18, 2006, the entire contents of both of which are hereby incorporated herein by reference.

BACKGROUND OF INVENTION

Melanoma is a common solid tumor notorious for its high rate of metastasis and resistance to chemotherapy and radiation. Several factors may account for the resistance of melanoma to current therapies. First, melanomas are derived from melanocytes, specialized neural crest cells that are specialized to produce melanin. The production of melanin results in the generation of toxic reactive oxygen species and cytotoxic phenol derivatives, thus melanocytes are equipped with mechanisms to resist these insults. Recently, the microopthalmia gene (MITF), which is a master transcriptional switch of melanocytes, has been shown to possess antiapoptotic activity and is found in metastatic lesions at a high frequency (25) (26). Second, multiple signaling pathways are activated in melanoma. B-raf is mutated in many melanomas, resulting in constitutive activation of MAP kinase signaling (1, 27). N-ras is also mutated frequently in melanoma, resulting in activation of MAP kinase, phosphoinositol-3 kinase/akt signaling, and S6 kinase activation (28, 29). While B-raf and constitutive MAP kinase activation is sufficient to cause transformation of melanocytes into melanoma (3, 4), other signal transduction events are frequently observed in B-raf mutant melanomas, such as loss of the tumor suppressor PTEN (29, 30). The consequences of PTEN loss is activation of phosphoinositol-3 kinase/akt activation.

Multiple regimens have been tried for the treatment of locally advanced and metastatic melanoma. Initial trials several decades ago used agents such as hydroxyurea, and more recent agents used against melanoma include dacarbazine and platinum based therapies including cisplatin and carboplatin. Other therapies, including biochemotherapy, have included interleukin-2 infusion and infusion of lymphocytes which are present in melanoma lesions and have been expanded ex vivo (31). All of these therapies have had modest success in a minority of patients, but with significant toxicity, including pulmonary leak syndrome (32-36). Currently, interferon alpha is employed in high risk patients, and prolonged therapy results in a 10% long term survival benefit.

Targeted therapies have been attempted in melanoma. Sorafenib was developed as a B-raf inhibitor based upon the observation that B-raf mutation is common in melanoma. However, results from initial trials of sorafenib in melanoma have been disappointing (15). Everolimus has also been tried against human melanoma, and has not been successful as a single agent (37). Current knowledge of signaling may provide an explanation of why previous therapies have failed. Phosphoinositol-3 kinase activation has been shown to mediate against extrinsic pathways of apoptosis, which include apoptosis due to TRAIL, TNF alpha, and interferons (38). Monotherapies of these cytokines may be frustrated in the face of phosphoinositol-3 kinase activation. Similarly, apoptosis induced by tumor infiltrating lymphocytes may be frustrated by phosphoinositol-3 kinase activation. Phosphoinositol-3 kinase also activates VEGF expression, and in addition to stimulating angiogenesis, VEGF inhibits dendritic cell function, impairing immune responses to melanoma (39-43).

Targeting MAP kinase as monotherapy in melanoma is clearly insufficient to eliminate melanoma in most patients. MAP kinase is activated in a majority of human melanomas, including those that lack B-raf mutation (3). In a previous study of human melanomas, we demonstrated that a subset of advanced melanomas had decreased MAP kinase activation, implying that additional signaling pathways are operative in vivo. Further support of this hypothesis is our previous finding that treatment of EBV-induced Burkitt's lymphomas with antioxidants resulted in compensatory MAP kinase activation (17). It is likely that treatment of melanoma patients with sorafenib results in compensatory activation of non-MAP kinase pathways. Similarly, mTOR inhibition due to rapamycin and derivatives has been shown to result in compensatory Akt activation (44).

Tris-DBA has the advantage that it inhibits several pathways required for melanoma tumorigenesis, including MAP kinase activation, phosphoinositol-3 kinase/akt activation, stat-3 activation, and S6 kinase activation. These pathways are involved in virtually all forms of human cancer, as well as autoimmune disorders, such as lupus, eczema (atopic dermatitis), asthma, psoriasis and arthritis. While no drug is likely to be completely effective as monotherapy in melanoma, Tris-DBA is well tolerated systemically in mice, and has a novel profile of action compared with other clinically used chemotherapeutic agents. Its ability to inhibit phosphoinositol-3 kinase activation may enhance the activity of cytokines which require akt inactivation for optimal activity, and may enhance the activity of other chemotherapeutic agents. Tris-DBA may also enhance the activity of sorafenib by blocking compensatory signaling that may occur in vivo due to MAP kinase blockade. Our studies provide a rationale for the further investigation of Tris-DBA in the treatment of malignant melanoma.

BRIEF SUMMARY OF THE INVENTION

Melanoma is one of the most common solid tumors and is notoriously difficult to treat. Recently, constitutive activation of several signaling pathways has been demonstrated in melanoma. Many melanomas carry mutations in B-raf, which cause constitutive activation of MAP kinase (1, 2). Even melanomas that do not carry activated B-raf demonstrate activation of MAP kinase, and constitutive expression of activated MAP kinase is sufficient to transform melanocytes to melanoma (3-5). Other pathways that are known to be activated in advanced melanoma include phosphoinositol-3 kinase/akt and nuclear factor kappa beta (NFκB) (6-10). All of these pathways confer survival and proliferative advantages to melanoma, such as induction of angiogenic factors, including vascular endothelial growth factor, interleukin-8, survivin, TAP, and mcl-2 (11-13).

Platinum compounds have been the mainstay of many solid tumor regimens, especially testicular cancer. However, platinum compounds, including cisplatin and carboplatin, have also shown activity in melanoma and have been incorporated into melanoma treatment regimens (14). Other inhibitors, such as sorafenib, a B-raf inhibitor, have had modest effects on melanoma with B-raf mutation despite robust inhibition of B-raf (15). This may be due to the ability of aggressive tumors to switch signaling pathways (16). We have observed this phenomenon in Burkitt's lymphoma, in which MAP kinase is activated when NFkB is downregulated (17). Similarly, inhibition of NFkB with velcade has had modest effects in melanoma (18, 19).

In our screens for angiogenesis inhibitors, we have identified a small molecule palladium complex which has structural similarities to curcumin and chalcones, compounds with known chemopreventive activity (20, 21). While chemopreventive agents are effective against preneoplastic agents in mice and man, they are less effective against established tumors (22, 23). We thus studied this novel palladium complex and found that it has activity against melanoma in vivo. Further preclinical evaluation of TrisDBA is warranted.

DETAILED DESCRIPTION OF THE INVENTION

Figure 1:
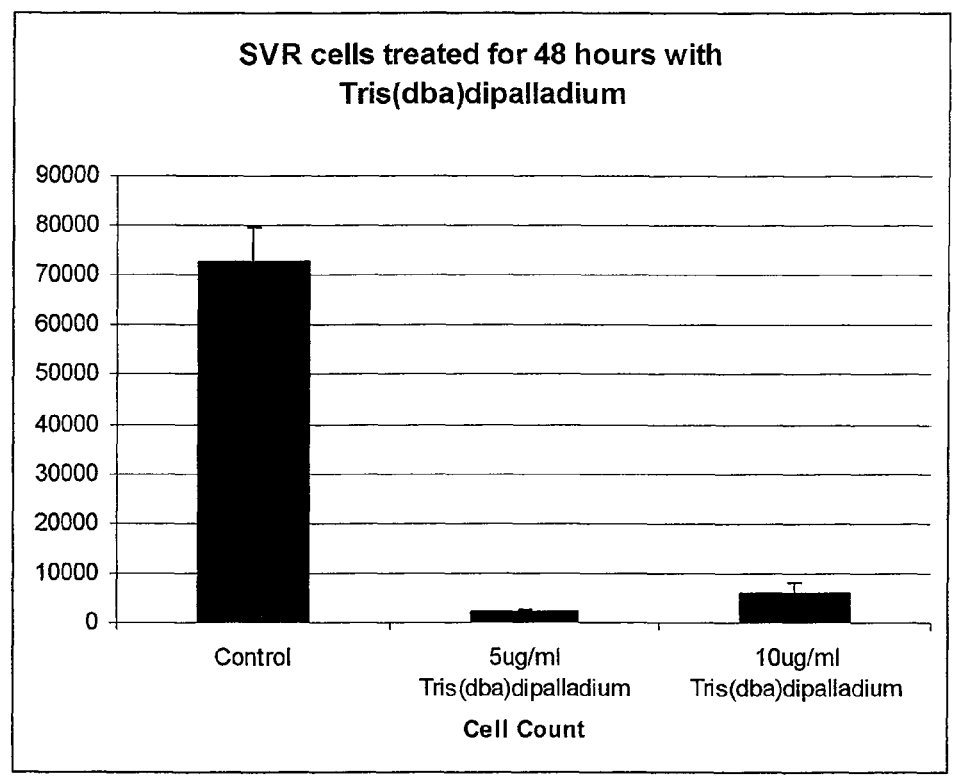
FIG. 1: Tris(dibenzylideneacetone)dipalladium inhibits angiogenesis in vitro. Tris(dba)dipalladium decreases SVR cell viability by over 90% at concentrations of 5 ug/ml and 10 ug/ml. Control is with the vehicle, DMSO. Each bar represents the average of triplicate experiments, and error bars reflect the standard error of the mean.

The following terms shall be used throughout the specification to describe the present invention.

The term "patient" is used throughout the specification to describe an animal, preferably a human, to whom treatment, including prophylactic treatment, with the compounds according to the present invention is provided. For treatment of those infections, conditions or disease states which are specific for a specific animal such as a human patient, the term patient refers to that specific animal. In most instances, the term patient refers to a human patient.

The term "effective amount" is used throughout the specification to describe concentrations or amounts of compounds according to the present invention which may be used to produce a favorable change in the disease or condition treated, whether that change is a remission, a decrease in growth or size of cancer, tumor or other growth, a favorable physiological result including the clearing up of skin or tissue, or the like, depending upon the disease or condition treated.

The term "angiogenesis" is used throughout the specification to describe the biological processes that result in the development of blood vessels or increase in the vascularity of tissue in an organism. With respect to the present invention, the term angiogenesis is defined as the process through which tumors or other rapidly proliferating tissue derive a blood supply through the generation of microvessels.

The term "tumor" is used to describe an abnormal growth in tissue which occurs when cellular proliferation is more rapid than normal tissue and continues to grow after the stimuli that initiated the new growth cease. Tumors generally exhibit partial or complete lack of structural organization and functional coordination with the normal tissue, and usually form a distinct mass of tissue that may be benign (benign tumor) or malignant (carcinoma). Tumors tend to be highly vascularized. The term "cancer" is used as a general term herein to describe malignant tumors or carcinoma. These malignant tumors may invade surrounding tissues, may metastasize to several sites and are likely to recur after attempted removal and to cause death of the patient unless adequately treated. As used herein, the terms carcinoma and cancer are subsumed under the term tumor.

The terms "angiogenic disease", "angiogenic disorder" and "angiogenic skin disorder" is used throughout the specification to describe a disorder, generally a skin disorder or related disorder which occurs as a consequence of or which results in increased vascularization in tissue. Oftentimes, the etiology of the angiogenic disease is unknown. However, whether angiogenesis is an actual cause of a disease state or is simply a condition of the disease state is unimportant, but the inhibition of angiogenesis in treating or reversing the disease state or condition is an important aspect of the present invention. Examples of angiogenic skin disorders which may be treated utilizing compounds according to the present invention include, for example, psoriasis, acne, rosacea, warts, seborrheic dermatitis, eczema (atopic dermatitis), hemangiomas and lymphangiogenesis, among numerous others, including Sturge-Weber syndrome, neurofibromatosis, tuberous sclerosis, chronic inflammatory disease and arthritis. Any skin disorder which has as a primary or secondary characterization, increased vascularization, is considered an angiogenic skin disorder for purposes of the present invention and is amenable to treatment with compounds according to the present invention.

The term "rosacea" is used to describe acne rosacea or erythematosa characterized by vascular and follicular dilation involving the nose and continguous portions of the cheeks. Rosacea may vary from very mild but persistent erythema to extensive hyperplasia of the sebaceous glands with deep-seated papules and pustules and accompanied by telangiectasia at the affected erythematous sites. Also called hypertrophic rosacea or rhinophyma, depending upon the severity of the condition.

The term "wart" is used to describe a small, usually hard tumerous growth on the skin. Also known as a verrucas, a wart is a flesh-colored growth of the skin which is characterized by circumscribed hypertrophy of the papillae of the corium, with thickening of the malpighian, granulation and keratin layers of the epidermis. Verucca vulgaris, a subset of warts or verruca, is characterized by infection of the keratinocytes with human papillomavirus.

The term "psoriasis" is used to describe a skin condition which is characterized by the eruption of circumscribed, discrete and confluent, reddish, silvery-scaled maculopapules;

the lesions occur preeminently on the elbows, knees, scalp and trunk and microscopically show characteristic parakeratosis and elongation of rete ridges.

The term "acne" is used to describe a condition of the skin characterized by inflammatory follicular, papular and pustular eruptions involving the sebaceous apparatus. Although there are numerous forms of acne, the most common form is known as acne simplex or acne vulgaris which is characterized by eruptions of the face, upper back and chest and is primarily comprised of comedones, cysts, papules and pustules on an inflammatory base. The condition occurs primarily during puberty and adolesence due to an overactive sebaceous apparatus which is believed to be affected by hormonal activity.

The term "eczema" is a generic term used to describe acute or chronic inflammatory conditions of the skin, typically erythematous, edematous, papular, vesicular, and crusting; followed often by lichenification and scaling and occasionally by duskiness of the erythema and, infrequently, hyperpigmentation. Eczema is often accompanied by the sensation of itching and burning. Eczema vesicles form by intraepidermal spongiosis. Eczema is sometimes referred to colloquially as tetter, dry tetter and scaly tetter. There are numerous subcategories of eczema, all of which are treated by one or more of the compounds according to the present invention. Another term for eczema is atopic dermatitis.

The compounds of the present invention are used to treat benign and malignant tumors, including various cancers such as, cervical, anal and oral cancers, stomach, colon, bladder, rectal, liver, pancreatic, lung, breast, cervix uteri, corpus uteri, ovary, prostate, testis, renal, brain/cns (e.g., gliomas), head and neck, eye or ocular, throat, skin melanoma, non-melanoma skin cancer and precursor lesions (including basal cell carcinoma, squamous cell carcinoma, and actinic keratosis), acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx, esophageal, larynx, kidney and lymphoma, among others. In addition, conditions such as neurofibromatosis, tuberous sclerosis (each of which conditions produces benign tumors of the skin), hemangiomas and lymphangiogenesis, among others, may be treated effectively with compounds according to the present invention.

Methods of treating tumors and/or cancer according to the present invention comprise administering to a patient in need thereof an effective amount of one or compounds according to the present invention.

A method of treating angiogenic skin disorders including psoriasis, acne, rosacea, warts and eczema, among numerous others, including Sturge-Weber syndrome, and related conditions using one or more of the disclosed compositions are other inventive aspects of the present invention. In addition, the present compounds may be used to treat venous ulcers of the skin as well. These methods comprise administering an effective amount of at least one compound according to the present invention to a patient in need of treatment or therapy.

Further inventive aspects of the present invention relate to the use of the present compositions in the treatment of arthritis and chronic inflammatory diseases, including rheumatoid arthritis and osteoarthritis, among others, including lupus and scleroderma. These methods also are directed to the administration of effective amounts of at least one compound according to the present invention to a patient in need of treatment or therapy.

Further aspects of the invention relate to the use of the contemplated compositions in the treatment of HIV. The HIV protein nef requires myristoylation for activity.

The compositions of the invention include small molecule palladium complexes having structural similarities to curcumin and chalcones with known chemoprotective activity. In particular, the invention contemplates Tris(dibenzylideneacetone) dipalladium and compositions comprising such a compound.

The compositions of the invention also include palladium complexes of curcuminoids and chalcone. Such curcuminoids and chalcones are well known and have been described in the literature including in U.S. Patent Pub. No. 2005/0148599 by Bowen, et al.; U.S. Pat. Pub. No. 2004/0176384 by Snyder et al.; and U.S. Pat. Nos. 6,673,843, 6,664,272 and 6,462,075 all of which are hereby incorporated by reference.

Pharmaceutical compositions based upon these novel chemical compounds comprise the above-described compounds in a therapeutically effective amount for the treatment of a condition or disease such as neoplasia, including cancer, an angiogenic skin disease or an inflammatory disease or a related condition or disease optionally in combination with a pharmaceutically acceptable additive, carrier or excipient.

Certain of the compounds, in pharmaceutical dosage form, may be used as prophylactic agents for preventing a disease or condition from manifesting itself. In certain pharmaceutical dosage forms, the pro-drug form of the compounds according to the present invention may be preferred.

The present compounds or their derivatives, including pro-drug forms of these agents, can be provided in the form of pharmaceutically acceptable salts. As used herein, the term pharmaceutically acceptable salts or complexes refers to appropriate salts or complexes of the active compounds according to the present invention which retain the desired biological activity of the parent compound and exhibit limited toxicological effects to normal cells. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, and polyglutamic acid, among others; (b) base addition salts formed with metal cations such as zinc, calcium, sodium; potassium, and the like, among numerous others.

Modifications of the active compound can affect the solubility, bioavailability and rate of metabolism of the active species, thus providing control over the delivery of the active species. Further, the modifications can affect the anti-angiogenesis activity of the compound, in some cases increasing the activity over the parent compound. This can easily be assessed by preparing the derivative and testing its activity according to known methods well within the routine skill in the art.

The compounds of this invention may be incorporated into formulations for all routes of administration including for example, oral, topical and parenteral including intravenous, intramuscular, eye or ocular, intraperitoneal, intrabuccal, transdermal and in suppository form.

Pharmaceutical compositions based upon these novel chemical compounds comprise the above-described compounds in a therapeutically effective amount for treating neoplasia, cancer and other diseases and conditions which have been described herein, including psoriasis, venous ulcers, acne, rosacea, warts, eczema, hemangiomas, lymphangiogenesis and chronic inflammatory diseases, including arthritis, among others, optionally in combination with a pharmaceutically acceptable additive, carrier and/or excipient. One of ordinary skill in the art will recognize that a therapeutically effective amount of one of more compounds according to the present invention will vary with the infection or condition to be treated, its severity, the treatment regimen to be employed, the pharmacokinetics of the agent used, as well as the patient (animal or human) treated.

In the pharmaceutical aspect according to the present invention, the compound according to the present invention is formulated preferably in admixture with a pharmaceutically acceptable carrier, excipient or additive. In general, it is preferable to administer the pharmaceutical composition in orally-administrable form, but for treatment of a number of conditions, a number of other formulations may be administered via a topical, parenteral, intravenous, intramuscular, transdermal, buccal, subcutaneous, suppository or other route, including an eye or ocular route. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect to the patient.

Pharmaceutically acceptable salt forms may be the preferred chemical form of compounds according to the present invention for inclusion in pharmaceutical compositions according to the present invention.

The amount of compound included within therapeutically active formulations according to the present invention is an effective amount for treating the infection or condition. In general, a therapeutically effective amount of the present preferred compound in dosage form usually ranges from slightly less than about 0.025 mg/kg to about 2.5 g/kg, preferably about 2.5-5 mg/kg to about 100 mg/kg of the patient or considerably more, depending upon the compound used, the condition or infection treated and the route of administration, although exceptions to this dosage range may be contemplated by the present invention. In its most preferred form, compounds according to the present invention are administered in amounts ranging from about 1 mg/kg to about 100 mg/kg. Where drug delivery is systemic rather than topical, this dosage range generally produces effective blood level concentrations of active compound ranging from less than about 0.04 to about 400 micrograms/cc or more of blood in the patient.

Administration of the active compound may range from continuous (intravenous drip) to several oral administrations per day (for example, Q.I.D.) and may include oral, topical, eye or ocular, parenteral, intramuscular, intravenous, subcutaneous, transdermal (which may include a penetration enhancement agent), buccal and suppository administration, among other routes of administration, including through an eye or ocular route.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral, topical or parenteral, including gels, creams ointments, lotions and time released implantable preparations, among numerous others. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

The present compounds may be used to treat animals, and in particular, mammals, including humans, as patients. Thus, humans and other animals, and in particular, mammals, suffering from tumors, and in particular, cancer, or other diseases as disclosed herein, can be treated by administering to the patient an effective amount of one or more of the compounds according to the present invention or its derivative or a pharmaceutically acceptable salt thereof optionally in a pharmaceutically acceptable carrier or diluent, either alone, or in combination with other known pharmaceutical agents (depending upon the disease to be treated). Treatment according to the present invention can also be administered in conjunction with other conventional cancer therapies, such as radiation treatment or surgery.

The active compound is included in the pharmaceutically acceptable carrier or diluent in an amount sufficient to deliver to a patient a therapeutically effective amount for the desired indication, without causing serious toxic effects in the patient treated.

The compound is conveniently administered in any suitable unit dosage form, including but not limited to one containing 1 to 3000 mg, preferably 5 to 500 mg of active ingredient per unit dosage form. An oral dosage of 10-250 mg is usually convenient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material-of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof may also be administered as a component of an elixir, suspension, syrup, wafer, chewing gum or the like. A syrup may contain, in addition to the active compounds, sucrose or fructose as a sweetening agent and certain preservatives, dyes and colorings and flavors.

The active compound or pharmaceutically acceptable salts thereof can also be mixed with other active materials that do not impair the desired action, or with materials that supplement the desired action, such as other anticancer agents, and in certain instances depending upon the desired therapy or target, antibiotics, antifungals, antiinflammatories, antiviral compounds or other agents having a distinct pharmacological effect.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic. If administered intravenously, preferred carriers include, for example, physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art. For example, liposomal formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

Numerous biological assays have been used and are accepted by those skilled in the art to assess the anti-tumor and anti-cancer activity of compounds according to the present invention. Any of these methods can be used to evaluate the activity of the compounds disclosed herein.

One common method of assessing activity is through the use of test panels of cancer cell lines. These tests evaluate the in vitro anti-cancer activity of particular compounds in cancer cell lines, and provide predictive data with respect to the use of tested compounds in vivo. Other assays include in vivo evaluations of the compound's effect on human or in an appropriate animal model, for example, using mouse tumor cells implanted into or grafted onto mice or in other appropriate animal models.

In the case of testing the anti-angiogenic/anti-cancer activity of compounds according to the present invention, an assay based on SVR cells may be employed. See, for example, Arbiser, et al., J. Am. Acad. Derm., pp. 925-929 (June, 1999). In this assay, SVR cells, which are derived from primary murine endothelial cells by the sequential introduction of SV40 large T antigen and activated H-ras according to the method of Arbiser, et al., Proc. Natl. Acad. Sci. USA 1997, 94: 861-6, are seeded onto a 24 well dish and treated with a compound according to the present invention at known concentration. The cell numbers are counted and compared against controls. Percent inhibition is readily determined from the data obtained. Other methods, well-known in the art, may also be used.

EXAMPLES

Cells

B16 cells (murine melanoma cells) and were cultured in Dulbeccos Modified Eagle Medium (1000 mg glucose/L, Sigma-Aldrich, St. Louis, Mo.) supplemented with 10% fetal bovine serum, L-glutamine (14 ml/L), and antibiotic/antimycotic (14 ml/L, Sigma-Aldrich). A 375 cells (murine melanoma cells) were cultured in Dulbeccos Modified Eagle Medium (4500 mg glucose/L, Sigma-Aldrich, St. Louis, Mo.) supplemented with 10% fetal bovine serum, L-glutamine (14 ml/L), and antibiotic/antimycotic (14 ml/L, Sigma-Aldrich).

Example 1

Cell Proliferation Assay

In order to evaluate the potential of tris(dibenzylideneacetone)dipalladium as an angiogenesis inhibitor, a proliferation assay was performed using SVR cells, an established murine model of angiogenesis (24). The assay was performed according to the method previously described by the Arbiser lab. Ten thousand SVR cells per well were plated in a 24-well plate. After incubation for twenty-four hours at 37 degrees and 5% CO2, the cells were treated with either 5 ug/mL or 10 ug/mL tris(dibenzylideneacetone)dipalladium or a control volume of DMSO. Treatment was from a stock solution of 10 mg/ml tris(dibenzylideneacetone)dipalladium dissolved in DMSO. The cells were allowed to incubate for an additional 48 hours and then were counted (FIG. 1). It was found that treatment with tris(dba)dipalladium for forty-eight hours significantly reduced the number of viable cells. A 5 ug/ml concentration of tris(dibenzylideneacetone)dipalladium resulted in a 97% decrease in cell count, while a 10 ug/ml concentration resulted in a 92% decrease (FIG. 1).

Example 2

Western Blot Analysis

We sought to determine the extent to which Tris(dibenzylidenacetone)dipalladium inhibits MAPK, Akt in murine melanoma model and pStat3, PS6 kinase in human melanoma model.

To examine this effect, we tested 10 μg/ml Tris(dba)dipalladium on MAPK and Akt signaling pathway using B16 melanoma cells. For signal transduction analysis, B16 cells, untreated and treated with 10 μg/ml tris(dibenzylideneacetone)dipalladium at timed intervals, were lysed in Nonidet P-40 lysis buffer (1% Nonidet P-40, 150 mM NaCl, 10% glycerol, 20 mM HEPES, 1 mM phenylmethylsulfonyl fluoride, 2.5 mM EDTA, 100 μM $Na_3VO_4$, and 1% aprotinin). The lysate was spun in microfuge, and the pellet was discarded. Protein concentration of the supernatant was determined by the Bradford assay using BSA as a standard. Samples were treated with Laemmli sample buffer and heated to 90° C. for 5 min before SDS-PAGE (National Diagnostics, Atlanta, Ga.) and was transferred to nitrocellulose membranes. The membranes were then blocked with 5% nonfat dry milk in 10 mM Tris/0.1% Tween 20/100 mM NaCl and were subsequently incubated with p42/44 MAP kinase antibody, Phospho-p44/42 MAP kinase (Thr202/Tyr204) antibody, Phospho-Akt (Ser-473) and Phospho-p70 S6 Kinase (Thr421/Ser424) antibody (Cell Signaling Laboratories, Beverly, Mass.). Monoclonal Anti-β-Tubulin antibody (Catalog number T0198, Sigma) was used as a loading control and detected using horseradish peroxidase-conjugated secondary antibody. The immunoreactive bands were visualized by enhanced chemiluminescence (Amersham Biosciences). Western blotting was performed as described by Liu et al (45) (FIGS. 2A and 2B).

Figure 2A:
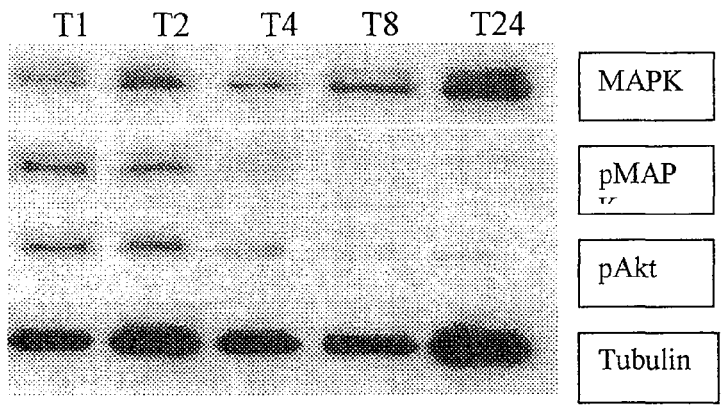
FIG. 2: Western blot analysis using Phosphorylated forms of MAPK, Akt (a), p70 S6kinase (b), Stat-3 (c). Western blot analysis of B16 and A 375 cells treated with 10 μg/ml Tris (dibenzylideneacetone)dipalladium at $T_1$, $T_2$, $T_4$, $T_8$, $T_{24}$. Cells were lysed and analyzed by using antibodies specific for the unphosphorylated form of MAPk, phosphorylated forms of MAPk, Akt, p70-S6kinase and Stat3. Tubulin was used as the loading control by using monoclonal anti β Tubulin antibody.
Figure 2B:
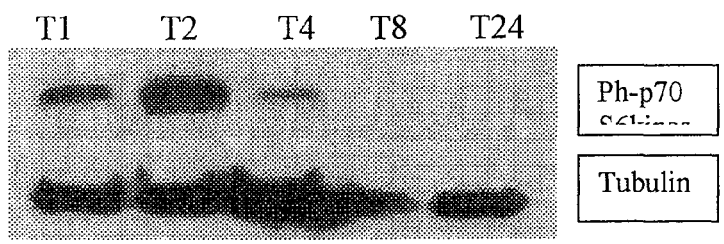
Figure 2C:
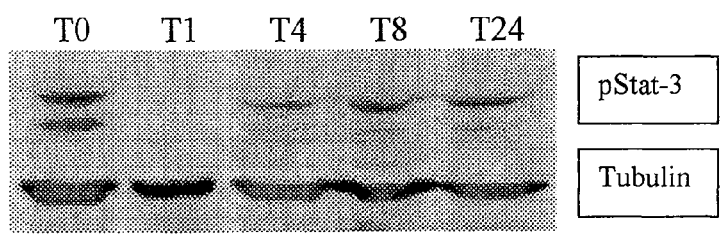

We found that Tris(dibenzylidenacetone)dipalladium inhibited the phosphorylated forms of both downstream (FIG. 2a). We further tested Tris(dba)dipalladium on human melanoma cell line and found that it inhibits phosphorylated forms of S 6 kinase downstream (FIG. 2b) and downregulates phospho-Stat-3 at shorter time intervals (1 and 4 hours) than after 24 hours of treatment (FIG. 2c)

Example 3

Quantitative RT-PCR for and VEGF in B 16 Cells and A375 Cells Treated with Vehicle Control and 10 μg/ml Tris(dibenzylideneacetone)dipalladium We performed RT-PCR to determine whether Tris(dibenzylidenacetone)dipalladium inhibits VEGF expression in murine and human melanoma cells in vitro.

Figure 3:
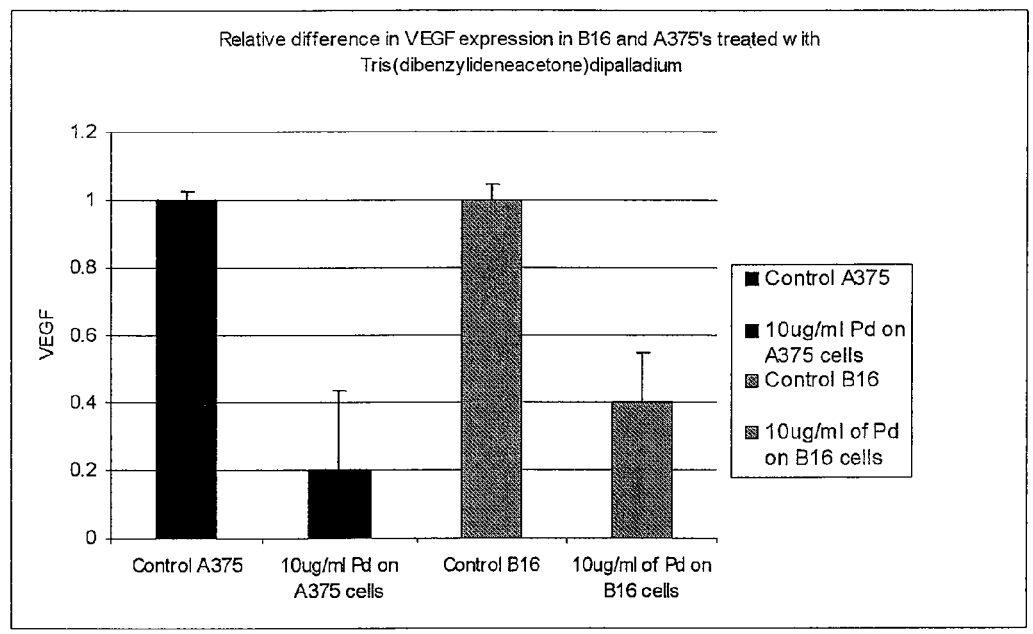
FIG. 3: Treatment of B16 and A375 cells with 10 μg/ml of Tris(dibenzylideneacetone)dipalladium decreases levels of VEGF mRNA (corrected for 18S RNA). Bars shown represent the average of triplicate experiments, and error bars indicate the standard error of the mean.

B 16 cells and A 375 cells were seeded equally into 2 T-25 flasks each and 24 hours later were treated with 0 and 10 μg/ml Tris(dibenzylideneacetone)dipalladium (Aldrich 328774) in DMSO for 24 hours. RNA was extracted and purified using TRIZOL (Sigma T 9424) and measured using spectrophotometer (Perkin-Elmer UV/VIS). 1 μg of RNA was used for DNase Amplification (Invitrogen Cat No. 18068-015) followed by First-Strand Synthesis for RT-PCR (SuperScript Cat No. 12371-019). 96-well Optical Reaction Plate (ABI PRISM, code 128) was used for the RT-PCR reaction. 2.5 μl of template, which had been diluted 1:10 in cross-linked water, was used in each well and the experiment was performed in triplicate. Vegfa (Applied Biosystems, Taqman Gene Expression Assay, Mm00437304_ml) and 18S (Applied Biosystems Taqman Gene Expression Assay, Hs99999901_s1) primers were used along with cross-linked molecular grade water (Cellgro) and master mix (Applied Biosystems TaqMan Fast Universal PCR Master Mix (2×)). Reaction was set up at the 7500 Applied Biosystems Reader for Absolute Quantification for 96 well plate. Ct values were analyzed by ΔΔCt method, and the standard error of the mean was calculated (FIG. 3)

When we tested 10 μg/ml Tris(dba)dipalladium on VEGF expression on B 16 cells and found a 60% decrease in VEGF expression compared to control. We further tested 10 μg/ml of the same compound on A 375 cells and found an 80% decrease compared to control (FIG. 3)

Example 4

In Vivo Tumor Growth

An experiment was performed to determine if tris(dibenzylideneacetone)dipalladium inhibits melanoma in vivo using murine melanoma models and human melanoma models.

Figure 4:
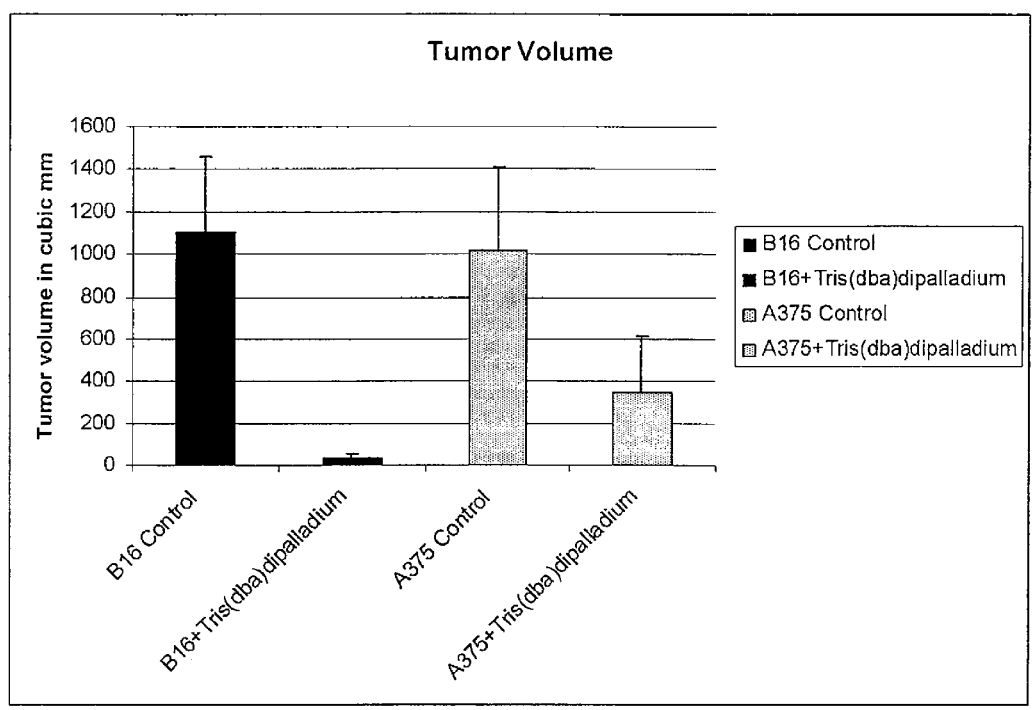
FIG. 4: Effect of Tris(dba)dipalladium in melanomas in vivo. Six mice were injected with 1,000,000 B16 and six mice with A375 cells and received intraperitoneal injection with Tris(dba)dipalladium and vehicle control. Animals were euthanized on day 15, secondary to tumor burden in the control animals. Photo above represents average tumor burden in each of the A 375 group and tumor volume (mm$^3$) is graphically depicted. Error bars represent the standard error of the mean.

In order to determine if compounds that inhibit VEGF, phosphorylated forms of MAPK, Akt, Stat 3 and p-70 S6 kinase in vitro would affect melanoma formation in vivo, we injected one million B16 cells subcutaneously into six nude mice and one million A 375 cells subcutaneously into six nude mice respectfully. Beginning two days later, the mice received intraperitoneal injections three times per week of either Tris(dibenzylideneacetone)dipalladium or control. 1 mg/mouse Tris(dba)dipalladium suspended in 0.3 ml peanut oil, and control was 0.3 ml peanut oil alone. Neither local nor systemic toxicity was observed in any of the nude mice as a result of treatment. A total of six rounds of injections were given over a period of two weeks, after which the mice were sacrificed due to overwhelming tumor burden in the control group. Animals were euthanized on day fifteen, secondary to tumor burden in the control animals. Graph represents average tumor volume ($mm^3$) in each of the two groups with controls (FIG. 4). Error bars represent the standard error of the mean.

Intraperitoneal treatment with either vehicle control and Tris(dibenzylideneacetone)dipalladium resulted in a 97.46% decreased tumor volume as compared to control when using the B 16 murine melanoma model. In the A 375 human melanoma model there was a 65.67% reduction in tumor volumes as compared to control (FIG. 4). Neither local nor systemic toxicity was observed in any of the nude mice as a result of treatment.

Example 5

N-Myristoyltransferase Assay

[$^3$H]Myristic acid (39.3 Ci/mmol) was obtained from NEN Life Science Products. *Pseudomonas* acyl CoA synthetase and coenzyme A were obtained from Sigma-Aldrich Canada. The peptide based on the $NH_2$-terminal sequence of the type II catalytic subunit of cAMP-dependent protein kinase (GNAAAAKKRR) was obtained from Alberta Peptide Institute, University of Alberta, Edmonton, Canada. The expression and purification of recombinant human NMT were undertaken as described previously (46). The NMT activity was measured as previously described (47,48). For the standard enzyme assays, the reaction mixture contained 0.4 µM [³H]myristoyl-CoA, 50 mM Tris-HCl, pH 7.8, 0.5 mM EGTA, 0.1% Triton X-100, 500 µM synthetic peptide and cell lysate as NMT source in a total volume of 25 µl. The reaction was initiated by the addition of radiolabeled [³H]myristoyl-CoA and incubated at 30° C. for 10-30 min. The reaction was terminated by spotting aliquots of incubation mixture onto P81 phosphocellulose paper discs and drying them under a stream of warm air. The P81 phosphocellulose paper discs were washed in three changes of 40 mM Tris-HCl, pH 7.3, for 90 min. The radioactivity was quantified in 7.5 ml of Beckman Ready Safe Liquid Scintillation mixture using a Beckman Liquid Scintillation Counter. One unit of NMT activity was expressed as 1 pmol of myristoyl-peptide formed per min per mg protein. The NMT1 inhibitory assay was carried out using various compounds according to the method described earlier (48).

Example 6

Tris(dibenzylideneacetone)dipalladium is an Inhibitor of N-myristoyltransferase

Figure 5:
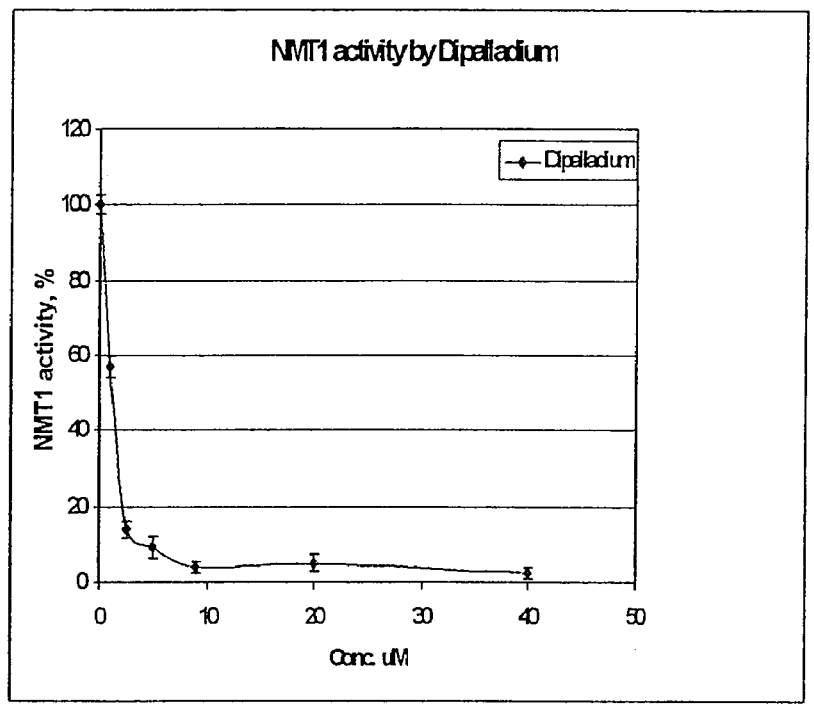
FIG. 5: Effect of Tris(dba)dipalladium on myristoyltransferase activity. Tris dba palladium is a potent inhibitor of NMT-1, with an inhibitory concentration (IC50) of approximately 1 micromolar.

Gene chip analysis of A375 human melanoma cells revealed that N-myristoyltransferase 1 was downregulated by treatment with Tris(dibenzylideneacetone)dipalladium. Since n-myristoyltransferase is required for the activation of upstream activators including stat-3, we hypothesized that inhibition of n-myristoyltransferase activity could lead to decreased levels of n-myristoyltransferase message as a downstream consequence. Thus, we tested the activity of Tris(dibenzylideneacetone)dipalladium as an NMT inhibitor. Potent inhibitory activity was observed, with an EC50 of 1 uM (FIG. 5).

REFERENCE

1. Pollock, P. M. and Meltzer, P. S. A genome-based strategy uncovers frequent BRAF mutations in melanoma, Cancer Cell, 2: 5-7, 2002.
2. Pollock, P. M., Harper, U. L., Hansen, K. S., Yudt, L. M., Stark, M., Robbins, C. M., Moses, T. Y., Hostetter, G., Wagner, U., Kakareka, J., Salem, G., Pohida, T., Heenan, P., Duray, P., Kallioniemi, O., Hayward, N. K., Trent, J. M. and Meltzer, P. S. High frequency of BRAF mutations in nevi, Nat. Genet., 33: 19-20, 2003.
3. Cohen, C., Zavala-Pompa, A., Sequeira, J. H., Shoji, M., Sexton, D. G., Cotsonis, G., Cerimele, F., Govindarajan, B., Macaron, N. and Arbiser, J. L. Mitogen-activated protein kinase activation is an early event in melanoma progression, Clin. Cancer Res., 8: 3728-3733, 2002.
4. Govindarajan, B., Bai, X., Cohen, C., Zhong, H., Kilroy, S., Louis, G., Moses, M. and Arbiser, J. L. Malignant transformation of melanocytes to melanoma by constitutive activation of mitogen-activated protein kinase kinase (MAPKK) signaling, J. Biol. Chem., 278: 9790-9795, 2003.
5. Sharma, A., Trivedi, N. R., Zimmerman, M. A., Tuveson, D. A., Smith, C. D. and Robertson, G. P. Mutant V599EB-Raf regulates growth and vascular development of malignant melanoma tumors, Cancer Res., 65: 2412-2421, 2005.
6. Dhawan, P. and Richmond, A. A novel NF-kappa B-inducing kinase-MAPK signaling pathway up-regulates NF-kappa B activity in melanoma cells, J. Biol. Chem., 277: 7920-7928, 2002.
7. Selzer, E., Thallinger, C., Hoeller, C., Oberkleiner, P., Wacheck, V., Pehamberger, H. and Jansen, B. Betulinic acid-induced Mc1-1 expression in human melanoma—mode of action and functional significance, Mol. Med., 8: 877-884, 2002.
8. Satyamoorthy, K., Li, G., Vaidya, B., Patel, D. and Herlyn, M. Insulin-like growth factor-1 induces survival and growth of biologically early melanoma cells through both the mitogen-activated protein kinase and beta-catenin pathways, Cancer Res., 61: 7318-7324, 2001.
9. Dhawan, P., Singh, A. B., Ellis, D. L. and Richmond, A. Constitutive activation of Akt/protein kinase B in melanoma leads to up-regulation of nuclear factor-kappaB and tumor progression, Cancer Res., 62: 7335-7342, 2002.
10. Soengas, M. S., Gerald, W. L., Cordon-Cardo, C., Lazebnik, Y. and Lowe, S. W. Apaf-1 expression in malignant melanoma, Cell Death. Differ., 13: 352-353, 2006.
11. Bhoumik, A., Gangi, L. and Ronai, Z. Inhibition of melanoma growth and metastasis by ATF2-derived peptides, Cancer Res., 64: 8222-8230, 2004.
12. Shattuck-Brandt, R. L. and Richmond, A. Enhanced degradation of I-kappaB alpha contributes to endogenous activation of NF-kappaB in Hs294T melanoma cells, Cancer Res., 57: 3032-3039, 1997.
13. Huang, S., DeGuzman, A., Bucana, C. D. and Fidler, I. J. Level of interleukin-8 expression by metastatic human melanoma cells directly correlates with constitutive NF-kappaB activity, Cytokines Cell Mol. Ther., 6: 9-17, 2000.
14. Karakousis, C. P., Getaz, E. P., Bjornsson, S., Henderson, E. S., Irequi, M., Martinez, L., Ospina, J., Cavins, J., Preisler, H., Holyoke, E. and Holtermann, O. cis-Dichlorodiammineplatinum(II) and DTIC in malignant melanoma, Cancer Treat. Rep., 63: 2009-2010, 1979.
15. Eisen, T., Ahmad, T., Flaherty, K. T., Gore, M., Kaye, S., Marais, R., Gibbens, I., Hackett, S., James, M., Schuchter, L. M., Nathanson, K. L., Xia, C., Simantov, R., Schwartz, B., Poulin-Costello, M., O'dwyer, P. J. and Ratain, M. J. Sorafenib in advanced melanoma: a Phase II randomised discontinuation trial analysis, Br. J. Cancer, 2006.
16 Arbiser, J. L. Molecular regulation of angiogenesis and tumorigenesis by signal transduction pathways: evidence of predictable and reproducible patterns of synergy in diverse neoplasms, Semin. Cancer Biol., 14: 81-91, 2004.
17. Cerimele, F., Battle, T., Lynch, R., Frank, D. A., Murad, E., Cohen, C., Macaron, N., Sixbey, J., Smith, K., Watnick, R. S., Eliopoulos, A., Shehata, B. and Arbiser, J. L. Reactive oxygen signaling and MAPK activation distinguish Epstein-Barr Virus (EBV)-positive versus EBV-negative Burkitt's lymphoma, Proc. Natl. Acad. Sci. U.S.A, 102: 175-179, 2005.
18. Markovic, S. N., Geyer, S. M., Dawkins, F., Sharfman, W., Albertini, M., Maples, W., Fracasso, P. M., Fitch, T., Lorusso, P., Adjei, A. A. and Erlichman, C. A phase II study of bortezomib in the treatment of metastatic malignant melanoma, Cancer, 103: 2584-2589, 2005.
19. Hamilton, A. L., Eder, J. P., Pavlick, A. C., Clark, J. W., Liebes, L., Garcia-Carbonero, R., Chachoua, A., Ryan, D. P., Soma, V., Farrell, K., Kinchla, N., Boyden, J., Yee, H., Zeleniuch-Jacquotte, A., Wright, J., Elliott, P., Adams, J. and Muggia, F. M. Proteasome inhibition with bortezomib (PS-341): a phase I study with pharmacodynamic end points using a day 1 and day 4 schedule in a 14-day cycle, J. Clin. Oncol., 23: 6107-6116, 2005.
20. Arbiser, J. L., Klauber, N., Rohan, R., van, L. R., Huang, M. T., Fisher, C., Flynn, E. and Byers, H. R. Curcumin is an in vivo inhibitor of angiogenesis, Mol. Med., 4: 376-383, 1998.
21. Robinson, T. P., Ehlers, T., Hubbard IV, R. B., Bai, X., Arbiser, J. L., Goldsmith, D. J. and Bowen, J. P. Design, synthesis, and biological evaluation of angiogenesis inhibitors: aromatic enone and dienone analogues of curcumin, Bioorg. Med. Chem. Lett., 13: 115-117, 2003.
22. Somasundaram, S., Edmund, N. A., Moore, D. T., Small, G. W., Shi, Y. Y. and Orlowski, R. Z. Dietary curcumin inhibits chemotherapy-induced apoptosis in models of human breast cancer, Cancer Res., 62: 3868-3875, 2002.
23. Khor, T. O., Keum, Y. S., Lin, W., Kim, J. H., Hu, R., Shen, G., Xu, C., Gopalakrishnan, A., Reddy, B., Zheng, X., Conney, A. H. and Kong, A. N. Combined inhibitory effects of curcumin and phenethyl isothiocyanate on the growth of human PC-3 prostate xenografts in immunodeficient mice, Cancer Res., 66: 613-621, 2006.
24. Bai, X., Cerimele, F., Ushio-Fukai, M., Waqas, M., Campbell, P. M., Govindarajan, B., Der, C. J., Battle, T., Frank, D. A., Ye, K., Murad, E., Dubiel, W., Soff, G. and Arbiser, J. L. Honokiol, a small molecular weight natural product, inhibits angiogenesis in vitro and tumor growth in vivo, J. Biol. Chem., 278: 35501-35507, 2003.
25. Garraway, L. A., Widlund, H. R., Rubin, M. A., Getz, G., Berger, A. J., Ramaswamy, S., Beroukhim, R., Milner, D. A., Granter, S. R., Du, J., Lee, C., Wagner, S. N., Li, C., Golub, T. R., Rimm, D. L., Meyerson, M. L., Fisher, D. E. and Sellers, W. R. Integrative genomic analyses identify MITF as a lineage survival oncogene amplified in malignant melanoma, Nature, 436: 117-122, 2005.
26. O'Reilly, F. M., Brat, D. J., McAlpine, B. E., Grossniklaus, H. E., Folpe, A. L. and Arbiser, J. L. Microphthalmia transcription factor immunohistochemistry: a useful diagnostic marker in the diagnosis and detection of cutaneous melanoma, sentinel lymph node metastases, and extracutaneous melanocytic neoplasms, J. Am. Acad. Dermatol., 45: 414-419, 2001.
27. Tuveson, D. A., Weber, B. L. and Herlyn, M. BRAF as a potential therapeutic target in melanoma and other malignancies, Cancer Cell, 4: 95-98, 2003.
28. Haluska, F. G., Tsao, H., Wu, H., Haluska, F. S., Lazar, A. and Goel, V. Genetic alterations in signaling pathways in melanoma, Clin. Cancer Res., 12: 2301s-2307s, 2006.
29. Tsao, H., Zhang, X., Benoit, E. and Haluska, F. G. Identification of PTEN/MMAC1 alterations in uncultured melanomas and melanoma cell lines, Oncogene, 16: 3397-3402, 1998.
30. Teng, D. H., Hu, R., Lin, H., Davis, T., Iliev, D., Frye, C., Swedlund, B., Hansen, K. L., Vinson, V. L., Gumpper, K. L., Ellis, L., El-Naggar, A., Frazier, M., Jasser, S., Langford, L. A., Lee, J., Mills, G. B., Pershouse, M. A., Pollack, R. E., Tornos, C., Troncoso, P., Yung, W. K., Fujii, G., Berson, A., Steck, P. A. and. MMAC1/PTEN mutations in primary tumor specimens and tumor cell lines, Cancer Res., 57: 5221-5225, 1997.
31. Legha, S. S. Durable complete responses in metastatic melanoma treated with interleukin-2 in combination with interferon alpha and chemotherapy, Semin. Oncol., 24: S39-S43, 1997.
32. Ahmadzadeh, M. and Rosenberg, S. A. IL-2 administration increases CD4+ CD25(hi) Foxp3+ regulatory T cells in cancer patients, Blood, 107: 2409-2414, 2006.
33. Maker, A. V., Yang, J. C., Sherry, R. M., Topalian, S. L., Kammula, U. S., Royal, R. E., Hughes, M., Yellin, M. J., Haworth, L. R., Levy, C., Allen, T., Mavroukakis, S. A., Attia, P. and Rosenberg, S. A. Intrapatient dose escalation of anti-CTLA-4 antibody in patients with metastatic melanoma, J. Immunother., 29: 455-463, 2006.
34. Margolin, K. A., Liu, P. Y., Unger, J. M., Fletcher, W. S., Flaherty, L. E., Urba, W. J., Hersh, E. M., Hutchins, L. E., Sosman, J. A., Smith, J. W., Weiss, G. R. and Sondak, V. K. Phase II trial of biochemotherapy with interferon alpha, dacarbazine, cisplatin and tamoxifen in metastatic melanoma: a Southwest Oncology Group trial, J. Cancer Res. Clin. Oncol., 125: 292-296, 1999.
35. Lewis, K. D., Gibbs, P., O'Day, S., Richards, J., Weber, J., Anderson, C., Zeng, C., Baron, A., Russ, P. and Gonzalez, R. A phase II study of biochemotherapy for advanced melanoma incorporating temozolomide, decrescendo interleukin-2 and GM-CSF, Cancer Invest, 23: 303-308, 2005.
36 Atkins, M. B. Cytokine-based therapy and biochemotherapy for advanced melanoma, Clin. Cancer Res., 12: 2353s-2358s, 2006.
37. Margolin, K., Longmate, J., Baratta, T., Synold, T., Christensen, S., Weber, J., Gajewski, T., Quirt, I. and Doroshow, J. H. CCI-779 in metastatic melanoma: a phase II trial of the California Cancer Consortium, Cancer, 104: 1045-1048, 2005.
38. Larribere, L., Khaled, M., Tartare-Deckert, S., Busca, R., Luciano, F., Bille, K., Valony, G., Eychene, A., Auberger, P., Ortonne, J. P., Ballotti, R. and Bertolotto, C. PI3K mediates protection against TRAIL-induced apoptosis in primary human melanocytes, Cell Death. Differ., 11: 1084-1091, 2004.
39. Burdelya, L., Kujawski, M., Niu, G., Zhong, B., Wang, T., Zhang, S., Kortylewski, M., Shain, K., Kay, H., Djeu, J., Dalton, W., Pardoll, D., Wei, S. and Yu, H. Stat3 activity in melanoma cells affects migration of immune effector cells and nitric oxide-mediated antitumor effects, J. Immunol., 174: 3925-3931, 2005.
40. Bromberg, J. Stat proteins and oncogenesis, J. Clin. Invest, 109: 1139-1142, 2002.
41. Arbiser, J. L., Moses, M. A., Fernandez, C. A., Ghiso, N., Cao, Y., Klauber, N., Frank, D., Brownlee, M., Flynn, E., Parangi, S., Byers, H. R. and Folkman, J. Oncogenic H-ras stimulates tumor angiogenesis by two distinct pathways, Proc. Natl. Acad. Sci. U.S.A, 94: 861-866, 1997.
42. Gabrilovich, D. I., Chen, H. L., Girgis, K. R., Cunningham, H. T., Meny, G. M., Nadaf, S., Kavanaugh, D. and Carbone, D. P. Production of vascular endothelial growth factor by human tumors inhibits the functional maturation of dendritic cells, Nat. Med., 2: 1096-1103, 1996.
43. Oyama, T., Ran, S., Ishida, T., Nadaf, S., Kerr, L., Carbone, D. P. and Gabrilovich, D. I. Vascular endothelial growth factor affects dendritic cell maturation through the inhibition of nuclear factor-kappa B activation in hemopoietic progenitor cells, J. Immunol., 160: 1224-1232, 1998.
44. Sarbassov, D. D., Ali, S. M., Kim, D. H., Guertin, D. A., Latek, R. R., Erdjument-Bromage, H., Tempst, P. and Sabatini, D. M. Rictor, a novel binding partner of mTOR, defines a rapamycin-insensitive and raptor-independent pathway that regulates the cytoskeleton, Curr. Biol., 14: 1296-1302, 2004.
45. Liu, A., Arbiser, J. L., Holmgren, A., Klein, G. and Klein, E. PSK and Trx80 inhibit B-cell growth in EBV-infected cord blood mononuclear cells through T cells activated by the monocyte products IL-15 and IL-12, Blood, 105: 1606-1613, 2005.
46. Raju, R. V., Moyana, T. N., and Sharma, R. K. Overexpression of human N-myristoyltransferase utilizing a T7 polymerase gene expression system. Protein Expr. Purif., 7: 431-437, 1996.
47. King, M. J., and Sharma, R. K. N-myristoyl transferase assay using phosphocellulose paper binding. Anal. Biochem., 199: 149-153, 1991.
48. King, M. J. and Sharma, R. K. (1993) Identification, purification and characterization of a membrane-associated N-myristoyltransferase inhibitor protein from bovine brain. Biochem. J. 291, 635-639.

What is claimed is:

1. A method of inhibiting angiogenesis in a mammal comprising administering to said mammal an effective amount of a small molecule palladium complex comprising at least one of a tris(dibenzylideneacetone)dipalladium, a chalcone and a curcuminoid to the mammal.

2. The method of claim 1 wherein the small molecule palladium complex comprises a Tris(dibenzylideneacetone) dipalladium.

3. The method of claim 1 wherein the small molecule palladium complex comprises a palladium complex of a chalcone.

4. The method of claim 1 wherein the small molecule palladium complex comprises a palladium complex of a curcuminoid.

5. The method according to claim 1 further comprises administering the effective amount to inhibit angiogenesis in the mammal with an angiogenic disorder selected from the group consisting of psoriasis, venous ulcers, acne, rosacea, warts, eczema, hemangiomas, lymphangiogenesis, Sturge-Weber syndrome, neurofibromatosis, tuberous sclerosis, chronic inflammatory disease and arthritis.

6. The method according to claim 1 further comprises administering the effective amount to inhibit angiogenesis in the mammal with a tumor selected from the group consisting of neurofibromatosis, tuberous sclerosis, hemangiomas and lymphangiogenesis and said cancer is selected from the group consisting of cervical, anal and oral cancers, eye or ocular cancer, stomach, colon, bladder, rectal, liver, pancreatic, lung, breast, cervix uteri, corpus uteri, ovary, prostate, testis, renal, brain/cns, head and neck, throat, skin melanoma, acute lymphocytic leukemia, acute myelogenous leukemia, Ewing's Sarcoma, Kaposi's Sarcoma, basal cell carcinoma and squamous cell carcinoma, actinic keratosis, small cell lung cancer, choriocarcinoma, rhabdomyosarcoma, angiosarcoma, hemangioendothelioma, Wilms Tumor, neuroblastoma, mouth/pharynx, esophageal, larynx, kidney and lymphoma.

7. The method according to claim 1 further comprises administering the effective amount to inhibit angiogenesis in the mammal with a cancer selected from the group consisting of cervical, anal and oral cancers, stomach, colon, bladder, rectal, liver, pancreatic, lung, breast, cervix uteri, corpus uteri, ovary, prostate, testis, renal, glioma, head and neck, eye or ocular, throat, skin melanoma, nonmelanoma skin cancer, basal cell carcinoma, squamous cell carcinoma, and actinic keratosis, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx, esophageal, larynx, kidney, lymphoma, neurofibromatosis, tuberous sclerosis and hemangioma.

8. The method according to claim 1 wherein the mammal is a human.

* * * * *

UNITED STATES PATENT AND TRADEMARK OFFICE
CERTIFICATE OF CORRECTION

| | | |
|---|---|---|
| PATENT NO. | : 8,030,299 B2 | Page 1 of 1 |
| APPLICATION NO. | : 12/470008 | |
| DATED | : October 4, 2011 | |
| INVENTOR(S) | : Jack Arbiser | |

It is certified that error appears in the above-identified patent and that said Letters Patent is hereby corrected as shown below:

In the Specification

Before the paragraph entitled Cross Reference to Related Applications, please insert the following sentences:

--This invention was made with U.S. government support under Grant Number AR047901 awarded by the National Institutes of Health. The U.S. government has certain rights in the invention.--

Signed and Sealed this
Seventeenth Day of January, 2017

Michelle K. Lee
*Director of the United States Patent and Trademark Office*

UNITED STATES PATENT AND TRADEMARK OFFICE
CERTIFICATE OF CORRECTION

| | |
|---|---|
| PATENT NO. | : 8,030,299 B2 |
| APPLICATION NO. | : 12/470008 |
| DATED | : October 4, 2011 |
| INVENTOR(S) | : Arbiser |

It is certified that error appears in the above-identified patent and that said Letters Patent is hereby corrected as shown below:

In the Specification

Column 1, after the priority information on Line 3, should read:
--"This invention was made with government support under grant AR047901 awarded by the National Institutes of Health. The government has certain rights in the invention."--

This certificate supersedes the Certificate of Correction issued January 17, 2017.

Signed and Sealed this
Sixteenth Day of April, 2024

Katherine Kelly Vidal
*Director of the United States Patent and Trademark Office*